United States Patent [19]
Knobel

[11] Patent Number: 5,705,062
[45] Date of Patent: Jan. 6, 1998

[54] ANALYTICAL DEVICE FOR SEPARATING MAGNETIC MICROPARTICLES FROM SUSPENSIONS

[75] Inventor: Rolf Knobel, Rotkreuz, Switzerland

[73] Assignee: Hoffmann-La Roche Inc., Nutley, N.J.

[21] Appl. No.: 301,857

[22] Filed: Sep. 7, 1994

[30] Foreign Application Priority Data

Sep. 17, 1993 [CH] Switzerland .............................. 2801/93

[51] Int. Cl.[6] .................................................. B01D 35/06
[52] U.S. Cl. .............................. 210/205; 210/222; 422/64; 422/100; 422/101
[58] Field of Search .................................... 210/222, 223, 210/205; 436/177, 178, 526; 422/101, 64, 100; 209/224, 232

[56]  References Cited

U.S. PATENT DOCUMENTS

| 4,502,958 | 3/1985 | Sasaki | 210/223 |
| 4,895,650 | 1/1990 | Wang | 210/222 |

FOREIGN PATENT DOCUMENTS

| 136 126 | 4/1985 | European Pat. Off. . | |
| 317 286 | 5/1989 | European Pat. Off. . | |
| 410 645 | 7/1990 | European Pat. Off. . | |
| 589 636 | 3/1994 | European Pat. Off. . | |
| 3 102 029 | 8/1982 | Germany . | |
| 22867 | 1/1992 | Japan | 436/526 |
| 92/05443 | 4/1992 | WIPO . | |

OTHER PUBLICATIONS

Derwent Abstract No. AN-82-72489E/35.

Derwent Abstract of Japan 04 022 867 (AN-92-077139/10).

*Primary Examiner*—Matthew O. Savage
*Attorney, Agent, or Firm*—George W. Johnston; William H. Epstein; John P. Parise

[57] ABSTRACT

An analytical device separates magnetic microparticles from a suspension. The separating portion of the device contains two permanent magnets between which the reaction vessel containing the suspension is disposed. For the purpose of more rapid, complete separation of the magnetic microparticles, magnets are positioned diametrically opposite one another relative to the reaction vessel. The polar axes of the magnets and the longitudinal axis of the reaction vessel include an acute angle.

15 Claims, 9 Drawing Sheets

ANALYTICAL DEVICE FOR SEPARATING MAGNETIC MICROPARTICLES FROM SUSPENSIONS

BACKGROUND OF THE INVENTION

1. Field

The invention relates to an analytical device capable of separating magnetic microparticles from suspensions contained within reaction vessels. The device is suitable for, among other things, use in a washing station of an analytical device for automatic immunoassays or for DNA detection.

2. Description

In many methods of analysis, including immunoassays, a solid phase has to be separated from a liquid phase and subsequently washed. To wash the solid phase, a defined amount of buffer solution is pipetted into the reaction vessel containing the solid phase to suspend the solid phase in the buffer solution. The solid and the liquid phase are then separated. The liquid phase is then removed by suction (aspiration) and a new washing process begins. Usually a number of washing cycles are carried out, each including a suspension, separation and aspiration process.

The use of magnetic microparticles as a solid phase and separation by permanent magnets is known in principle. Permanent magnets attract the microparticles to the wall of the reaction vessel and hold them there.

European patent application EP 0 136 126 describes a device for separation during solid-phase immunoassays. The bottom end of a reaction vessel containing magnetic particles are disposed between two permanent magnets. The axes of magnetization are at right angles to the wall of the reaction vessel, thus reducing stray magnetic fields.

International application WO 92/05443 describes a device for separating magnetic microparticles. The reaction vessels containing the magnetic particles are disposed in rows. Between the rows is positioned a magnetic block. The reaction vessels are disposed between the magnetic block such that two magnets-are diametrically opposite relative to the reaction vessel. The magnets have alternating polarities and their magnetization axes extend parallel. Separated particles are on only one side of the reaction vessel.

German Offenlegungsschrift DE 31 02 029 describes a device for separating ferromagnetic particles from suspensions using permanent magnets disposed at only one side of the reaction vessel. The magnet is adapted to the shape of the vessel and includes an acute angle with the longitudinal axis of the vessel. The magnetization axis is at fight angles to the wall of the vessel.

U.S. Pat. No. 4,895,650, the contents of which is herein incorporated by reference, describes a separating device in which microparticles are separated by a permanent magnet. The magnet is on only one side of the reaction vessel. The relation between the level of test solution in the test-tube and the position of the magnet is focused on. The position of the magnet, more particularly its height, must coincide with the level of test solution in the reaction vessel, and is brought to the desired height by packing material in the bottom part of the device holding the magnet.

During an immunoassay, the fluid level in the reaction vessels after adding the required reagents is not necessarily uniform. For example, the level in the reaction vessel after adding conjugate solution may be lower than the level after adding washing buffer solution. The method of analysis described in U.S. Pat. No. 4,895,650 does not take these differences in level into account.

Known devices for separating magnetic microparticles have the disadvantage of requiring a relatively long time before all microparticles are separated from the liquid phase. Separation time may be considerable, particularly for larger volumes.

A device for rapid separation of magnetic microparticles is described in European patent application EP 317 286. In this device the reaction vessel is surrounded by four permanent magnets (magnets 1, 2, 3 and 4), which are uniformly distributed around a reaction vessel. The direction of the magnetic field of magnets 1 and 3 is rotated through 180° relative to the direction of the magnetic field of magnets 2 and 4. This device has the disadvantage of requiring a relatively large number of permanent magnets to speed up separation. It also excludes many possible cell movements.

An aim of the subject invention is to provide an analytical device comprising a device for separating magnetic microparticles such that the magnetic microparticles in suspension can be rapidly separated even when the reaction vessel is filled to different levels. Another aim is to provide an analytical device for separating magnetic microparticles such that the magnetic microparticles in suspension can be separated in a focused manner.

SUMMARY OF THE INVENTION

The subject invention provides an analytical device comprising at least one station for receiving a reaction vessel containing a suspension of magnetic microparticles in a solution. The station contains means for separating the magnetic microparticles from the solution. The means comprises diametrically opposite magnets between which the reaction vessel is disposed, the polar axes of each magnet forming an acute angle with the longitudinal axis of the reaction vessel. Preferably, the acute angle is about 45°.

In the above analytical device, the magnets may be connected by a holder having a groove into which the base of the reaction vessel projects. Typically, the magnets each have a top surface and are disposed so that the top surface of each magnet lies below the surface of the suspension, the polar axes of the two magnets intersecting at the suspension surface. The magnets each have a north pole and a south pole can be alternatively disposed so that north poles and south poles of the magnets lie near the base of the reaction vessel, the polar axes of the diametrically opposite magnets intersecting near the base of the reaction vessel. For all of the above devices, the at least one station generally comprises from about 1 to about 20 receiving stations radially disposed on a circular rotor magazine.

Preferably, the rotor magazine is a part of a washing device which normally comprises (i) at least one processing station for separating a solid from a liquid; (ii) at least one processing station for aspiring a liquid; and (iii) at least one processing station for suspending a solid within a liquid. Each station may contain a receiving station for separating the magnetic microparticles from solution. Each receiving station preferably includes diametrically opposite magnets each having a top surface. The magnets are disposed so that the top surface of each magnet lies below the surface of the suspension, the polar axes of the two magnets intersecting at the suspension surface. Alternatively, each receiving station may include diametrically opposite magnets each having a north pole and a south pole disposed so that the north poles and the south poles of the magnets lie near the base of the reaction vessel, with the polar axes of the two magnets intersecting near the base of the reaction vessel.

Receiving stations in a circular rotor magazine each typically contain a pair of magnets disposed along radii of the rotor which are at an acute angle to each other, typically at an angle of about 20°. In such a device, the rotor magazine is often times rotatably mounted on a shaft which is rotated by a toothed belt drive by a driving motor actuated in cyclic manner so that each reaction vessel comes to rest in each receiving station.

BRIEF DESCRIPTION OF THE FIGURES

FIG. 7—A perspective view of an analytical device.

DETAILED DESCRIPTION OF THE INVENTION

The subject invention will now be described in terms of its preferred embodiments. These embodiments are set forth to aid in the understanding of the subject invention, but are not to be construed as limiting.

The subject invention provides an analytical device containing the following components: at least one station for receiving a reaction vessel containing a suspension of magnetic microparticles, the station containing a device for separating magnetic microparticles, and the separating device comprising two magnets between which the reaction vessel is disposed, characterized in that the magnets are diametrically opposite relative to the reaction vessel and the polar axes of the magnets and the longitudinal axis of the reaction vessel include an acute angle.

Preferably the polar axes of the magnets and the longitudinal axis of the reaction vessel include an angle of about 45°.

The magnets can be connected to a holder formed with a groove into which the bottom of the reaction vessel projects.

The magnets, relative to the reaction vessel containing a suspension, can be disposed so that the polar axes of the magnets intersect near the surface of the suspension or near the base of the reaction vessel. The surface of the suspension is the level to which the reaction vessel is filled after adding the washing buffer solution. The stations for receiving the reaction vessels, according to the invention, are stations in a washing device. However, the separating device according to the invention can be used in all receiving stations in an analytical device where a solid phase is separated from a liquid phase.

The washing device preferably comprises a rotatable circular rotor magazine and a holder bearing a resuspension and aspiration device. Six processing stations, uniformly distributed on a rotor magazine, are advantageously disposed in a washing device. However, other arrangements of the processing stations are possible. The washing devices can contain processing stations for separating a solid from a liquid phase and comprising arrangements of magnets, and processing stations for resuspension and without an arrangement of magnets. Each magnet arrangement advantageously comprises two pairs of magnets between which the reaction vessel is disposed. Each magnet arrangement therefore comprises two receiving stations. The magnets in the receiving stations can be disposed along radii relative to the diameter of the circular rotor magazine. Each pair of receiving stations can be adjacent so that the radii along which their magnets are disposed include an acute angle of e.g. about 20°.

The main advantages of the invention are that, owing to the special alignment of the polar axes with intersection of the polar axes near the surface of the suspension, the magnetic lines of force of the total field of force extend so that the stray magnetic field is also used to separate the magnetic microparticles. Even when the reaction vessel is filled to the maximum height, the magnetic microparticles at the surface of the suspension are within the range of influence of the total field of force and can be rapidly and completely separated from the suspension. After the magnetic microparticles have been separated, the upper limit of the separated microparticles on opposite walls of the reaction vessel is always below the level of liquid when reagent or washing solutions are added during the test.

When the polar axes are aligned with intersection near the base of the reaction vessel, the magnetic microparticles in suspension can be separated in a focused manner on opposite walls of the reaction vessel. This version is suitable to separate magnetic particles having a high degree of magnetic parts (magnetism). This version makes possible to obtain a more intensive mixing with subsequently added liquid.

The analytical device according to the invention can achieve a maximum output, i.e. a maximum number of samples processed per unit time in a plant of given size, using minimum means and with optimum reliability.

The separation process in a washing station is a time factor in the process. According to the invention, this time factor is reduced in that a) the receiving stations contain two permanent magnets disposed diametrically opposite relative to the reaction vessel and with specially aligned polar axes, b) a number of reaction vessels are simultaneously subjected to a separation process, and c) the reaction vessels are supplied stepwise to the resuspension or aspiration processes.

The cycle times of all the processing stations are adjusted to one another so as to avoid idle times.

By way of example, the drawings show an analytical device for automatic solid-phase immunoassays. In such immunoassays, the solid phase containing magnetic microparticles is separated from the liquid phase by permanent magnets. After separation, the microparticles are deposited on two diametrically opposite regions on the wall of the reaction vessel.

Figure 1:
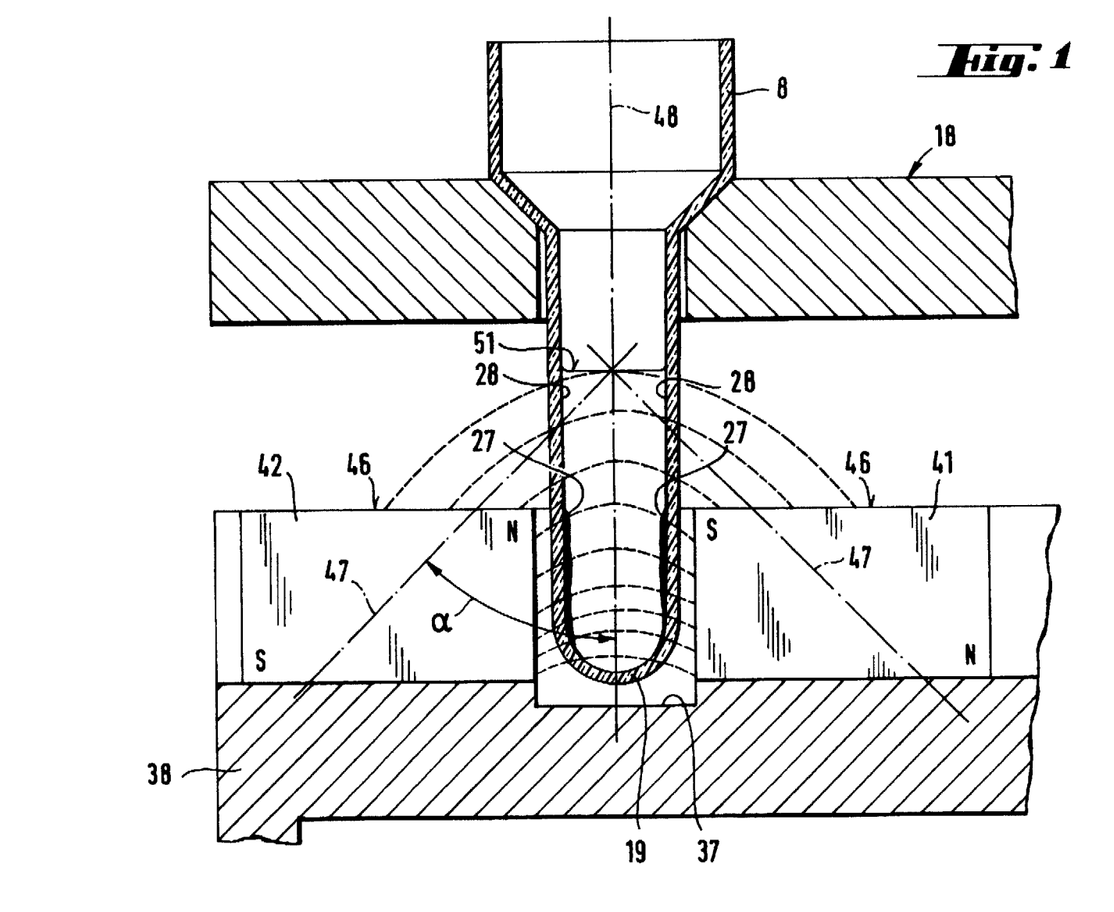
FIGS. 1 and 8—Illustration of a section through a receiving station containing a separating device and an arrangement of magnets according to the invention.

FIG. 1 shows a station for receiving a reaction vessel containing a suspension of magnetic microparticles, the station containing a device for separating magnetic microparticles and the separating device comprising two magnets between which the reaction vessel is disposed, characterized in that the magnets 41 and 42 are diametrically opposite relative to the reaction vessel 8, and the polar axes 47 of the magnets 41 and 42 and the longitudinal axis 48 of the reaction vessel 8 include an acute angle ($\alpha$). The angle ($\alpha$) is about 45°.

Magnets 41 and 42 are connected by a holder 38 formed with a groove 37 into which the bottom 19 of the reaction vessel 8 projects.

The magnets 41, 42 and the holder 38 are parts of a receiving station in a rotor magazine 18.

The top edge 46 of the magnets 41 and 42 is below the suspension surface 51 at which the polar axes 47 of magnets 41 and 42 intersect. The magnetic microparticles 27 are deposited at two diametrically opposite wall regions 28 inside the reaction vessel 8, nearest the magnets 41 and 42. Deposits form in a locally restricted region, thus ensuring that when the height to which the reaction vessel is filled varies during the test, the level of liquid is always above the deposit 27 and consequently resuspension can be reliably carried out.

Figure 2:
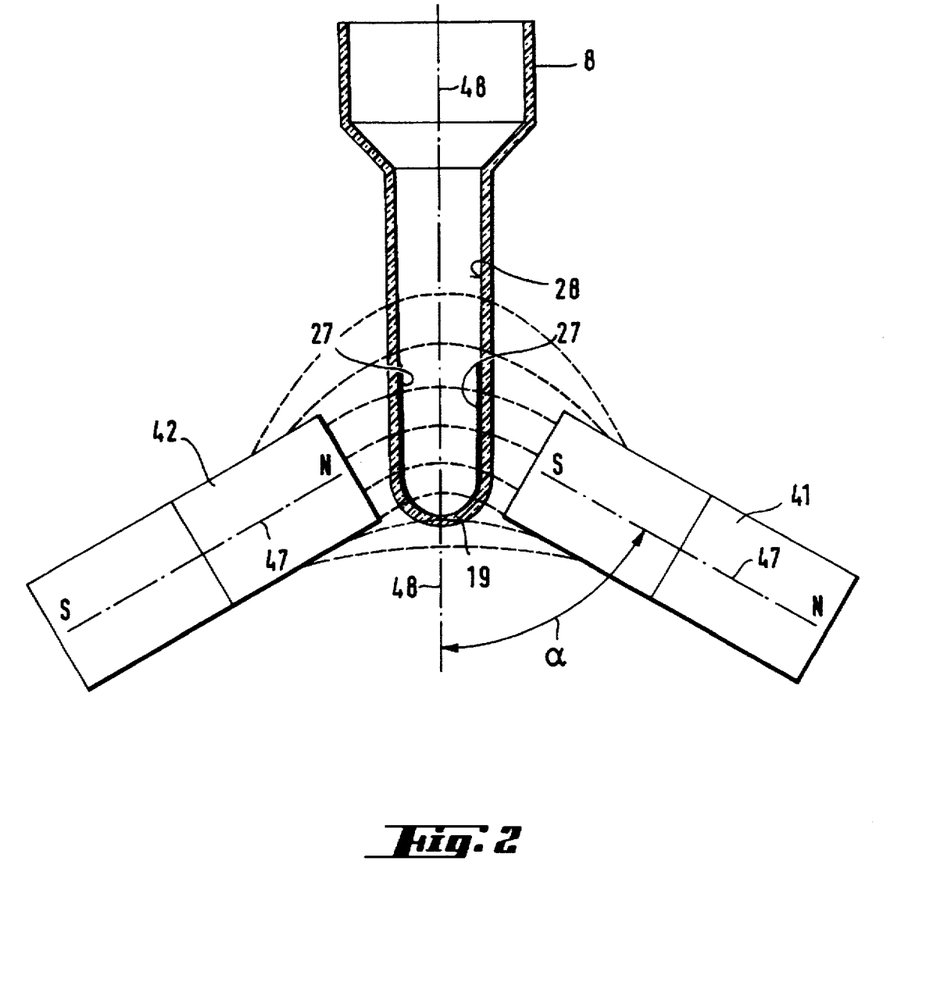
FIGS. 2 and 9—Illustration of a reaction vessel within the influence of a magnetic field of force.

FIG. 2 shows the deposits of magnetic microparticles 27 on the inner wall 28 of the reaction vessel 8 within the influence of a magnetic field, when the magnets 41 and 42 are differently arranged according to the invention. The lines of force of the individual magnets are diagrammatically shown. The angle ($\alpha$) between the polar axis 47 and the longitudinal axis 48 of the reaction vessel 8 is about 60°.

Figure 3:
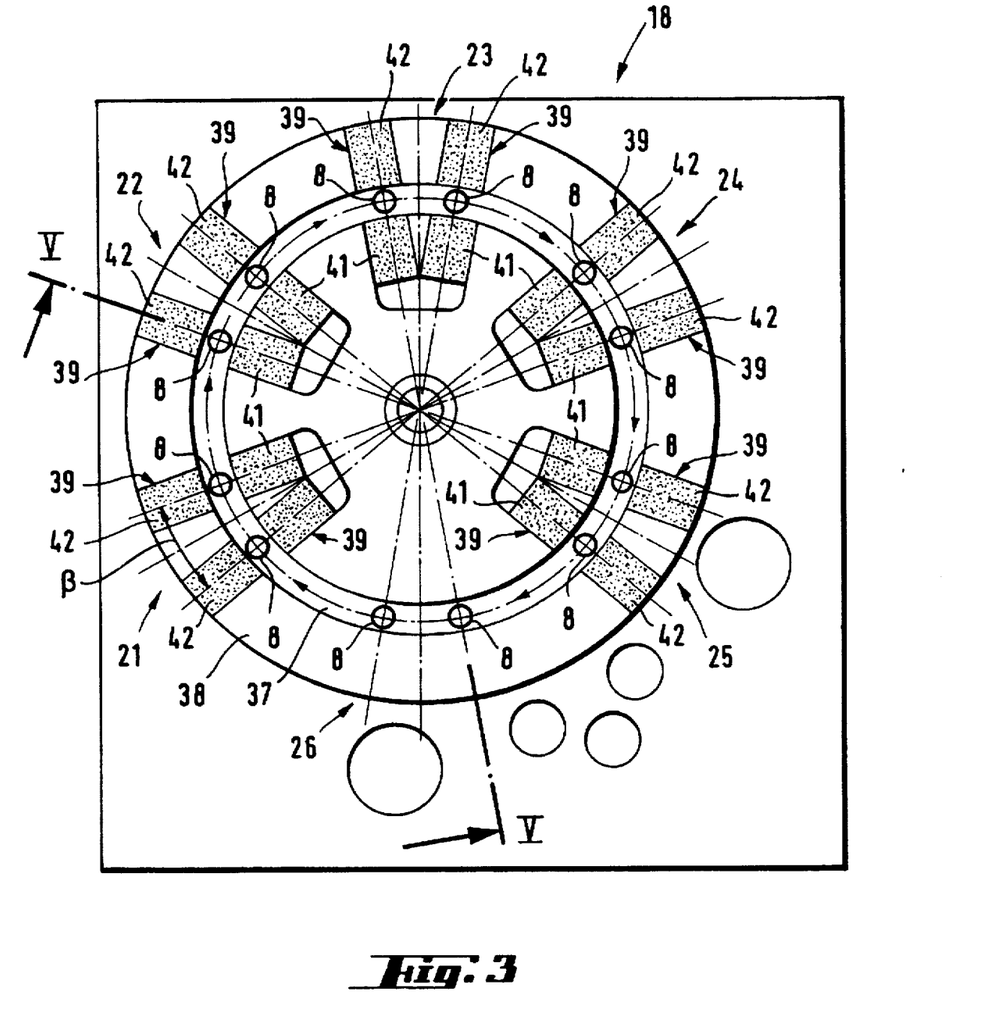
FIG. 3—Illustration of the radial arrangement of the processing stations of a circular rotor magazine.

FIG. 3 shows six processing stations 21-26 radially disposed on a circular rotatable rotor magazine 18, the processing stations 21-24 being used to separate the solid from the liquid phase, and aspiration being brought about in station 25 and resuspension in station 26, the stations 21-25 containing devices for separating the magnetic microparticles. Stations 21-25 each contain a magnet arrangement 39 comprising two pairs of magnets. Both versions (according FIG. 1 containing the magnets 41, 42 and according FIG. 8 containing the magnets 61, 62) are possible. The magnets 41, 42, relative to the diameter of the circular rotor magazine 18, being disposed along radii at an acute angle ($\beta$). The angle ($\beta$) is about 20°. Between magnets 41 and 42, the reaction vessels 8 are disposed in the groove 37 of the magnet holder 38. The magnet arrangements 39 are spaced apart by angles of about 60°.

Figure 4:
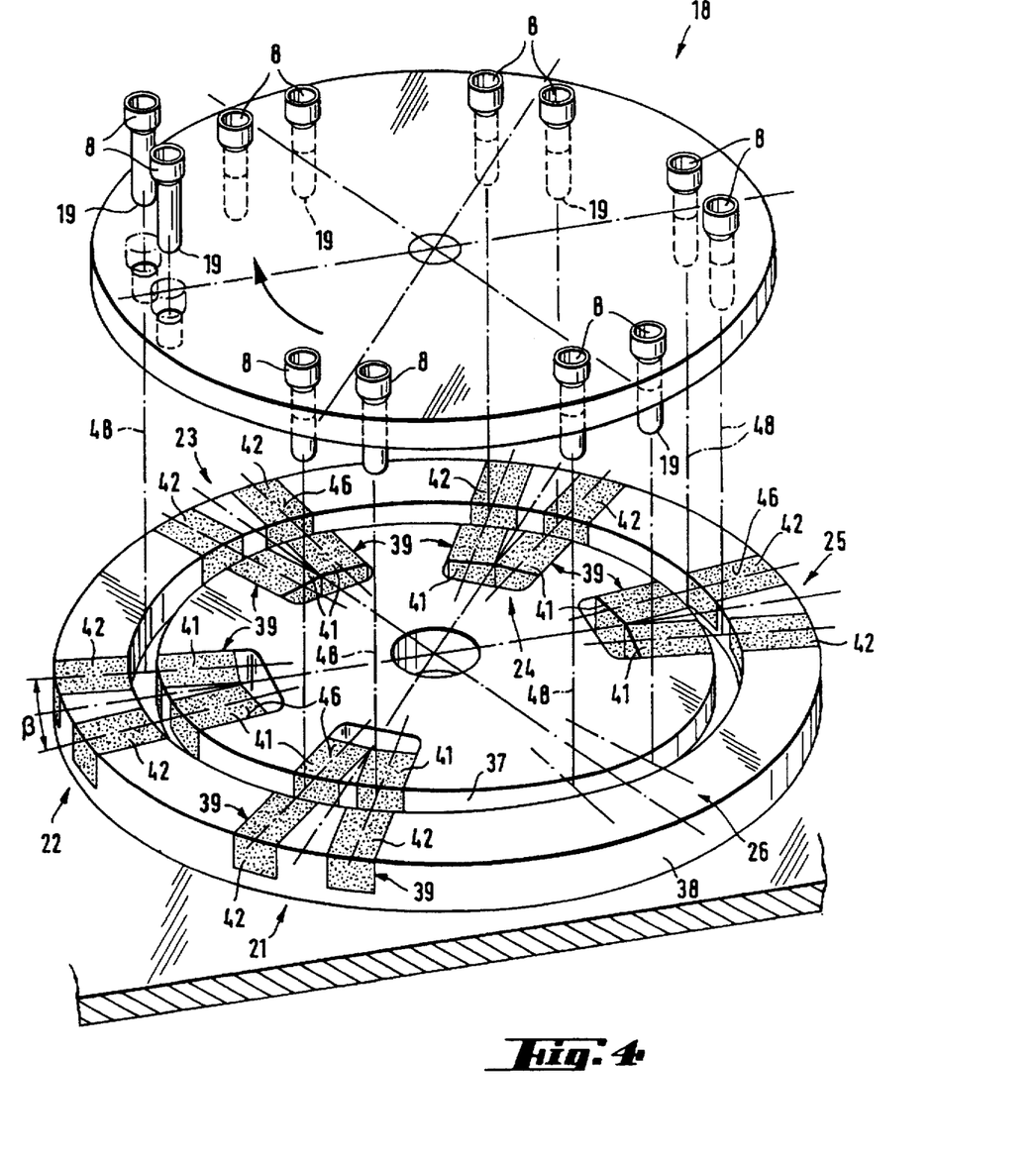
FIG. 4—A general view of a rotor magazine.

FIG. 4 is a perspective general view of the rotor magazine 18, showing the processing stations 21-26. As can be seen, the longitudinal axes 48 of the reaction vessels 8 extend parallel to the axis of rotation of the rotor. The base 19 of the reaction vessels 8 lies above the groove 37 of the magnet-holder 38. Twelve reaction vessels 8 are disposed in six pairs on a common pitch circle in the edge region of the rotor 18. Each pair is separated from the others by an angle of about 60°.

Figure 5:
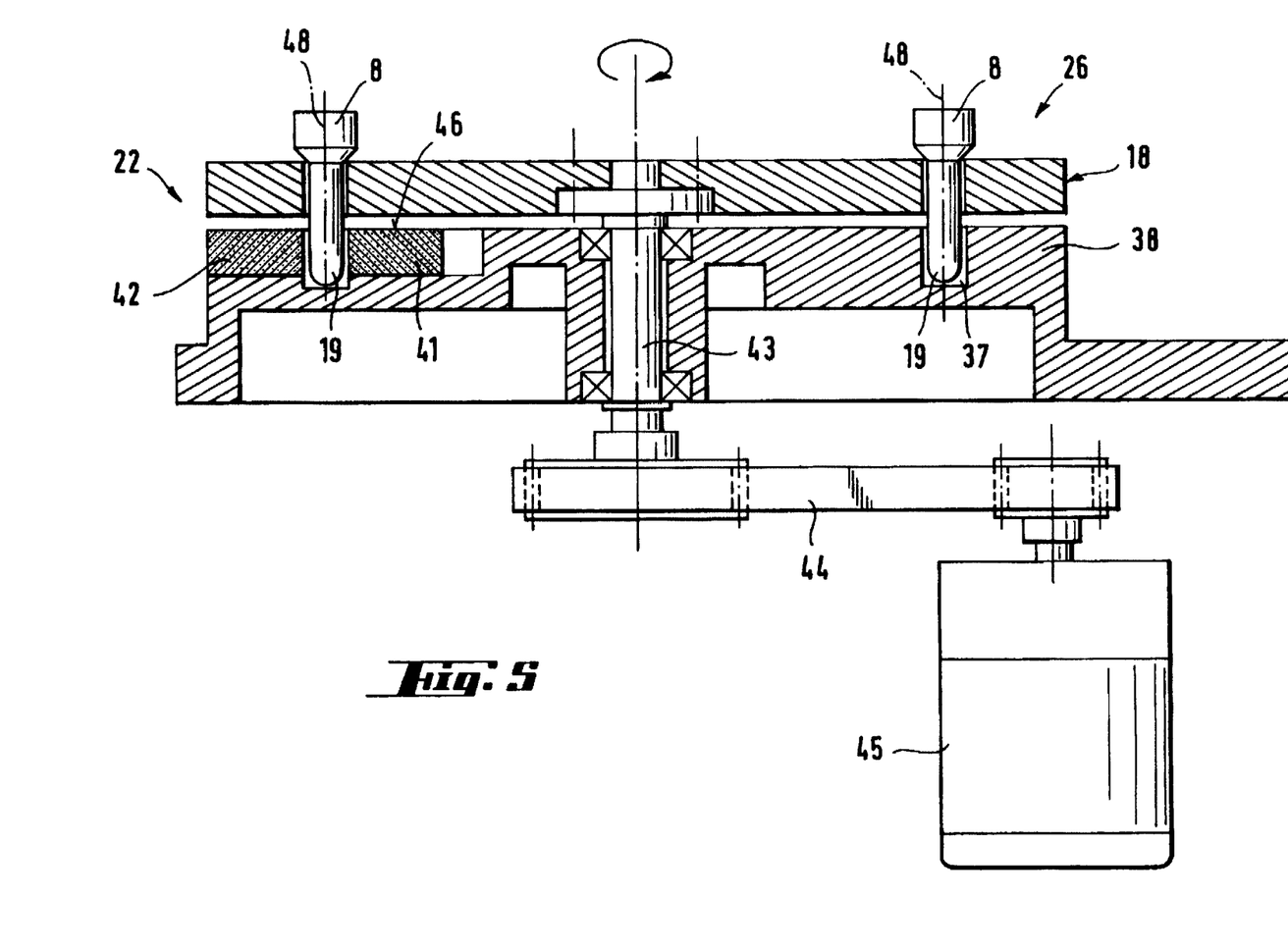
FIG. 5—Sectional view through a separating device along line V—V in FIG. 3.

FIG. 5 is a section through a separating device from station 22 to 26, comprising the reaction vessels 8. The longitudinal axes of the reaction vessels 8 extend parallel to the axis of rotation of the rotor. The processing station 22 contains magnets 41 and 42 whereas station 26 does not contain any magnets and is for resuspending the magnetic microparticles. The rotor magazine 18 is connected to a driving motor 45 via a toothed belt drive 44 and a shaft 43 mounted in the magnet-holder 38.

The motor 45 can be actuated in cyclic manner so that the reaction vessels 8 each come to rest at the corresponding processing stations, as long as required by the processes. During each transfer cycle, the rotor magazine rotates through about 30°. Since the arrangement of magnets in the different stations is always the same, the magnetic microparticles always collect at identical regions on the inner wall of the reaction vessel.

Figure 6:
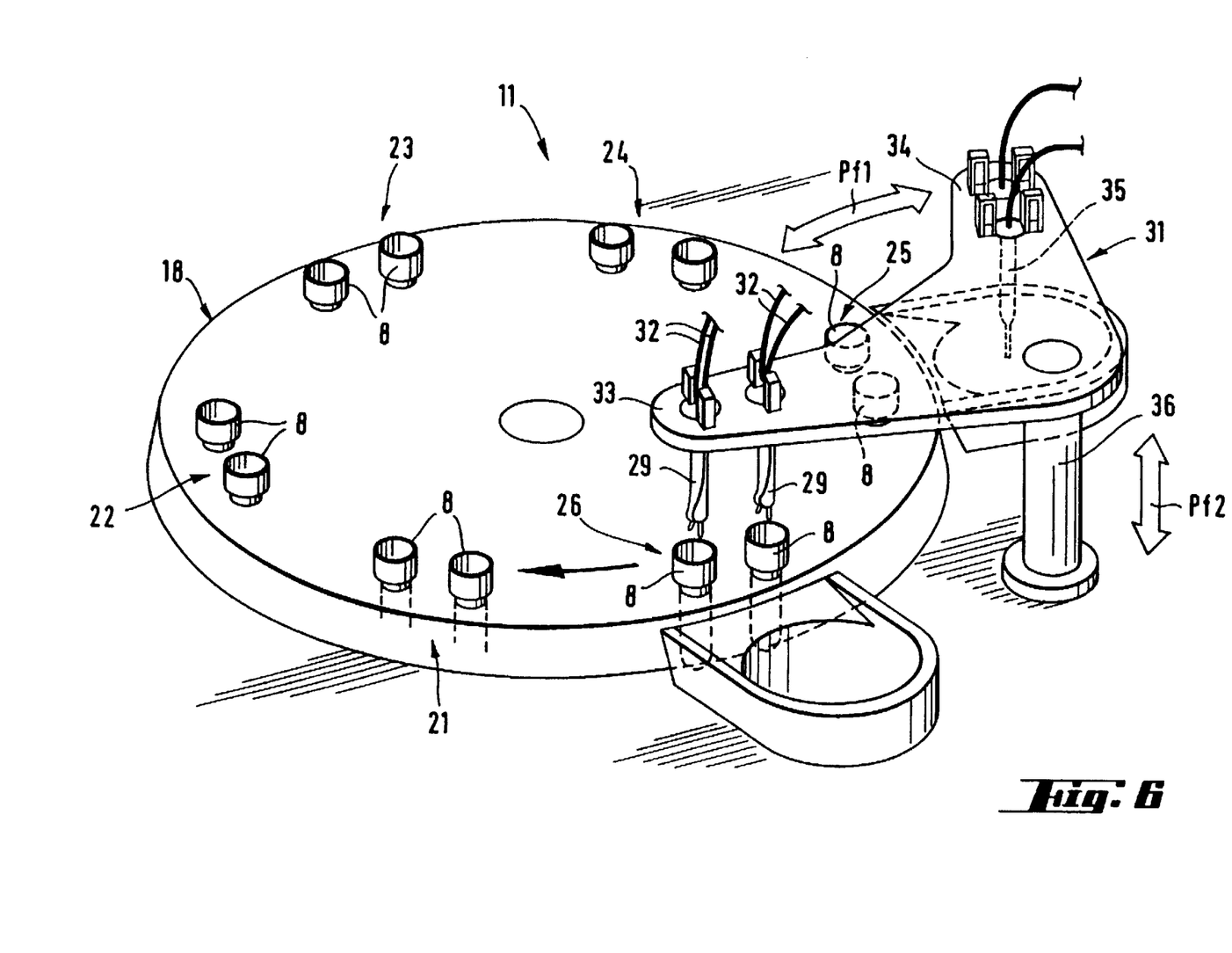
FIG. 6—General View of the washing device.

FIG. 6 shows a washing device 11 according to the invention, containing a rotor magazine 18 and a holder 31 with a resuspension and aspiration device, and showing the processing stations 21-26 as before.

The aspiration and resuspension devices in stations 25 and 26 are secured to a holder 31 and connected by capillary tubes 32 to a supply system (pump, storage containers, etc). The holder 31 is a two-armed lever, the injection nozzles 29 being disposed at one end 33 of the levers and the hollow aspiration needles 35 being disposed on the other lever arm 34. The lever arm is pivotable around an axis of rotation 36 and can be vertically lowered. This adjustment is shown by arrows Pf1, Pf2 in FIG. 6. The amount of angular adjustment, the distance between the injection and aspiration elements and their arrangement on the corresponding lever ends of the holder are adapted to one another so that the injection elements 29, for the purpose of processing, can be brought into alignment with the reaction vessels 8 in the processing station 26 or the aspiration needles 35 can be brought into alignment with the vessels 8 in the processing stations 25. Elements not in the working position are disposed over a draining container.

FIG. 7 is a general view of the analytical device according to the invention, designed, e.g., for performance of DNA detections. The device 1 contains means for performing the aforementioned immunoassays, i.e. in the present case two racks 3, 4 with reagents on a vibrating table 5, three racks 7 with throwaway reagent containers 8, a temperature-controlled incubator 9, a washing device 11 and a photometer 12.

The samples, reagents, and reagent vessels are transferred by a transfer head 13 movable in an x-y coordinate system and comprising a pipetting device 14 and a reaction vessel gripper 15, both movable in the z direction.

The washing device can be loaded and unloaded via the gripper 15 in the transfer device 13.

Process parameters can be input via a control panel 16 and/or a bar code wand 17. The CPU controls and coordinates all processes.

Figure 8:
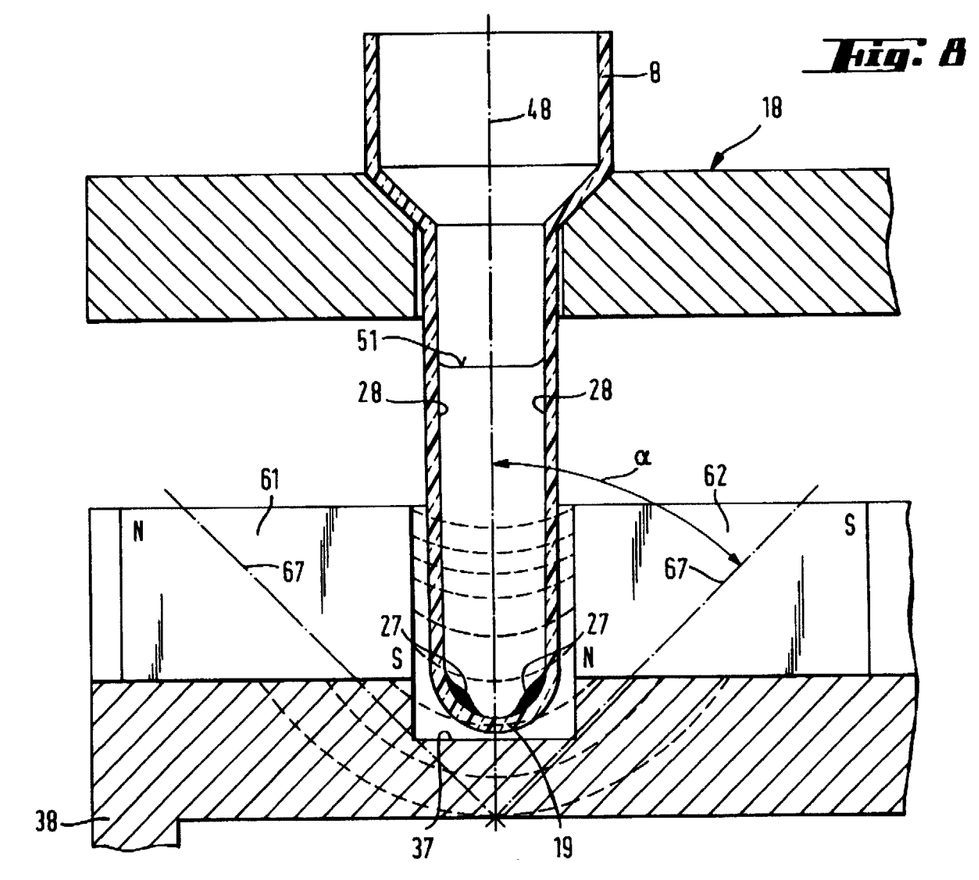

FIG. 8 shows as well as FIG. 1 a station for receiving a reaction vessel containing a suspension of magnetic microparticles, the station containing a device for separating magnetic microparticles and the separating device comprising two magnets between which the reaction vessel is disposed. The difference to FIG. 1 is that the magnets 41 and 42 shown in FIG. 1 are rotated through about 180°. North and south poles of the magnets 61 and 62 are positioned near the base 19 of the reaction vessel 8 diametrically opposite relative to the reaction vessel 8. The polar axes 67 of the magnets 61 and 62 and the longitudinal axis 48 of the reaction vessel 8 include an acute angle ($\alpha$) and intersect near the base 19 of the reaction vessel 8. The angle ($\alpha$) is about 45°.

Magnets 61 and 62 are connected by a holder 38 formed with a groove 37 into which the bottom 19 of the reaction vessel 8 projects.

The magnets 61, 62 and the holder 38 are parts of a receiving station in a rotor magazine 18.

The magnetic microparticles 27 are deposited at two diametrically opposite wall regions 28 inside the reaction vessel 8, in a focused manner.

Figure 9:
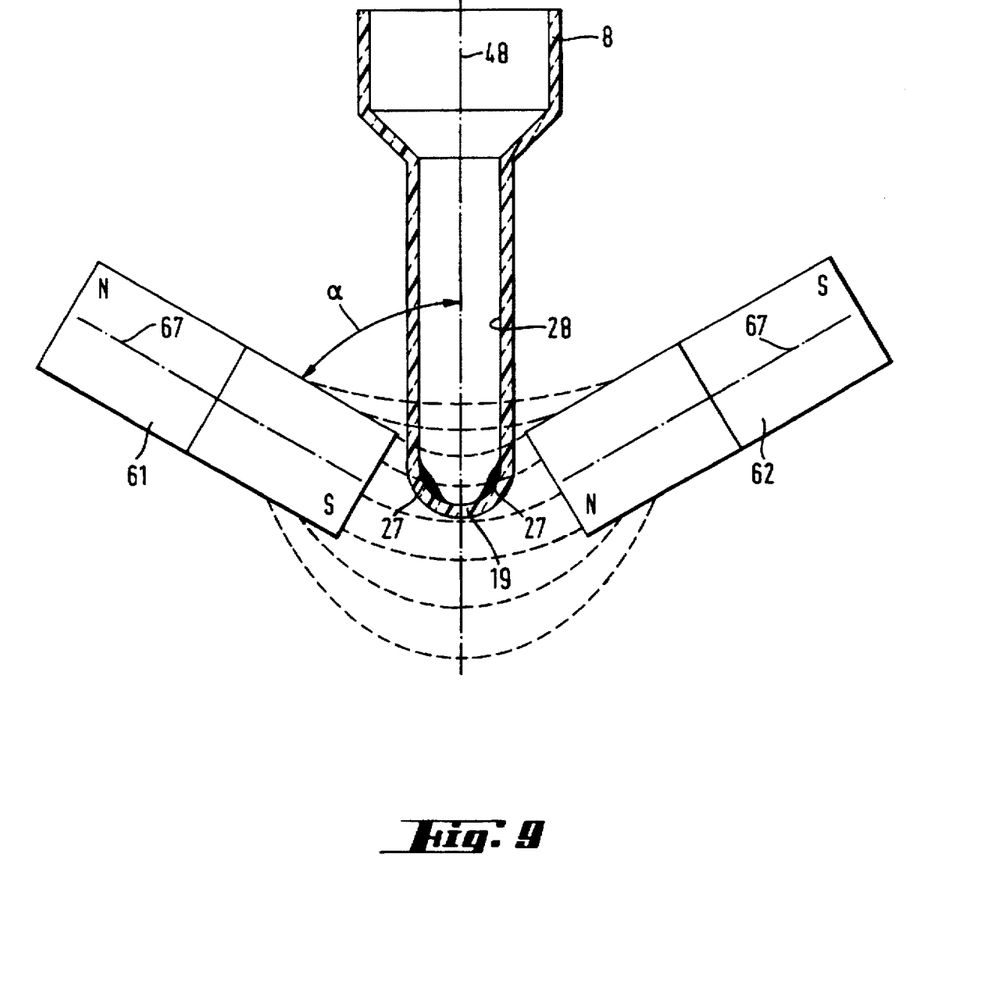

FIG. 9 shows the deposits of magnetic microparticles 27 on the inner wall 28 of the reaction vessel 8 within the influence of a magnetic field, when the magnets 61 and 62 are differently arranged according to the invention. The lines of force of the individual magnets are diagrammatically shown. The angle ($\alpha$) between the polar axis 67 and the longitudinal axis 48 of the reaction vessel 8 is about 60°.

The invention has been described in terms of its preferred embodiments. Upon reading the present specification, numerous alternative embodiments will become obvious to one skilled in the art. For example, angles, number of stations, etc. can be varied by the skilled artisan. These variations are to be considered within the scope and spirit of the subject invention, which is only to be limited by the claims which follow and their equivalents.

What is claimed is:

1. An analytical device which comprises:
   (a) a reaction vessel having an elongated body with a longitudinal portion, a closed base and a longitudinal axis of symmetry, the reaction vessel containing a suspension of magnetic microparticles in solution, the suspension having a free surface; and
   (b) at least one receiving station having means for receiving the reaction vessel and means for separating the magnetic microparticles from the solution when the reaction vessel is received by the receiving station, the means for separating the magnetic microparticles comprising a pair of magnets, each magnet in the pair being diametrically opposite to the other magnet in the pair and arranged so that the longitudinal portion of the reaction vessel when received by the receiving station is located between the magnets, each of the magnets having a polar axis which intersects with the polar axis of the other magnet at a point on the longitudinal axis of the reaction vessel, each of the polar axes forming an acute angle with the longitudinal axis of the reaction vessel.

2. The device according to claim 1, wherein the acute angle is about 45°.

3. The device according to claim 1, wherein the magnets are connected to a holder having a groove into which the base of the reaction vessel projects.

4. The device according to claim 1, wherein the magnets each have a top surface and are disposed so that the top surface of each magnet lies below the free surface of the suspension, the polar axes of the two magnets intersecting at the free surface of the suspension.

5. The device according to claim 1, wherein the magnets each have a north pole and a south pole, and are disposed so that the north pole of one of the magnets and the south pole of the diametrically opposite magnet lie near the base of the reaction vessel, the polar axes of the diametrically opposite magnets intersection with each other near the base of the reaction vessel.

6. The device according to claim 1, wherein the device comprises from about 1 to about 20 receiving stations disposed on a circular rotor magazine, and the pair of magnets of each receiving station is radially disposed with respect to the circular rotor magazine.

7. The device according to claim 6, wherein the rotor magazine is a part of a washing device, the washing device comprising (i) at least one processing station for separating a solid from a liquid; (ii) at least one processing station for aspirating a liquid; and (iii) at least one processing station for suspending a solid within a liquid, each processing station containing the receiving station including two of the diametrically opposite magnets each having a top surface and being disposed so that the top surface of each magnet lies below the free surface of the suspension, the polar axes of the two magnets intersecting with each other at the free surface of the suspension.

8. The device according to claim 7, wherein the pair of magnets of the first receiving station is disposed along a first radius, the pair of magnets of the second receiving station in the immediate vicinity of the first receiving station is disposed along a second radius, and the first and second radii form an acute angle with each other.

9. The device according to claim 8, wherein the acute angle is about 20°.

10. The device according to claim 6, wherein the rotor magazine is a part of a washing device, the washing device comprising (i) at least one processing station for separating a solid from a liquid; (ii) at least one processing station for aspirating a liquid; and (iii) at least one processing station for suspending a solid within a liquid, each processing station containing the receiving station for separating the magnetic microparticles from solution, each receiving station including two of the diametrically opposite magnets each having a north pole and a south pole, the magnets being disposed so that the north pole of one of the magnets and the south pole of the diametrically opposite magnet lie near the base of the reaction vessel, the polar axes of the two magnets intersecting with each other near the base of the reaction vessel.

11. The device according to claim 10, wherein the pair of magnets of the first receiving station is disposed along a first radius, the pair of magnets of the second receiving station in the immediate vicinity of the first receiving station is disposed along a second radius, and the first and second radii form an acute angle with each other.

12. The device according to claim 11, wherein the acute angle is about 20°.

13. The device according to claim 6, wherein the pair of magnets of the first receiving station is disposed along a first radius, the pair of magnets of the second receiving station in the immediate vicinity of the first receiving station is disposed along a second radius, and the first and second radii form an acute angle with each other.

14. The device according to claim 13, wherein the acute angle is about 20°.

15. The device according to claim 6, wherein the rotor magazine is rotatably mounted on a shaft, and wherein the device further comprises a driving motor connected to the shaft by a toothed belt, and means for cyclically actuating the driving motor, so that when the driving motor is actuated in a cyclic manner each reaction vessel comes to rest in each receiving station.

* * * * *